(12) United States Patent
Tenhuisen et al.

(10) Patent No.: US 7,636,998 B2
(45) Date of Patent: Dec. 29, 2009

(54) URETHRAL STENT REDUCER

(75) Inventors: Kevor Tenhuisen, Randolph, NJ (US);
Joseph H. Contiliano, Stewartsville, NJ
(US); David W. Overaker, Annandale,
NJ (US)

(73) Assignee: Ethicon, Inc., Somerville, NJ (US)

( * ) Notice: Subject to any disclaimer, the term of this patent is extended or adjusted under 35 U.S.C. 154(b) by 1068 days.

(21) Appl. No.: 10/748,059

(22) Filed: Dec. 29, 2003

(65) Prior Publication Data
US 2005/0149162 A1 Jul. 7, 2005

(51) Int. Cl.
*B23P 11/00* (2006.01)
*B21D 39/00* (2006.01)
(52) U.S. Cl. ........................................ 29/516
(58) Field of Classification Search ................. 606/108; 623/1.11, 1.12, 1.23; 29/516, 517, 700
See application file for complete search history.

(56) References Cited

U.S. PATENT DOCUMENTS

| 5,160,341 | A | | 11/1992 | Brenneman et al. |
| 5,246,445 | A | | 9/1993 | Yachia et al. |
| 5,476,505 | A | | 12/1995 | Limon |
| 5,928,238 | A | * | 7/1999 | Scarborough et al. .......... 606/79 |
| 6,019,779 | A | * | 2/2000 | Thorud et al. ................ 606/198 |
| 6,042,606 | A | * | 3/2000 | Frantzen ..................... 623/1.18 |
| 6,413,269 | B1 | * | 7/2002 | Bui et al. .................... 623/1.11 |
| 6,451,025 | B1 | * | 9/2002 | Jervis .......................... 606/108 |
| 2002/0151967 | A1 | * | 10/2002 | Mikus et al. ................ 623/1.22 |

FOREIGN PATENT DOCUMENTS

SU 1754094 A1 8/1992

OTHER PUBLICATIONS

U.S. Appl. No. 10/602,338; "Biodegradable Stent"; Filed Jun. 24, 2003; Inventors: Datta, Huxel, Jamiolkowski and Li.

* cited by examiner

*Primary Examiner*—Julian W Woo
*Assistant Examiner*—Dianne Dornbusch

(57) ABSTRACT

An apparatus for compressing a coiled stent having at least one protrusion, such as an enlarged coil disposed at the end of the stent, has a mandrel insertable into a lumen of the stent for holding the stent by friction and a coil compressor coupled to the mandrel. The mandrel is rotatable on an axis relative to the coil compressor and the coil compressor has a tab extending therefrom towards the mandrel. A stent is placed on the mandrel with the enlarged coil extending toward the coil compressor. The tab presses the enlarged coil inwardly toward the lumen of the stent when the mandrel is rotated relative to the coil compressor.

12 Claims, 5 Drawing Sheets

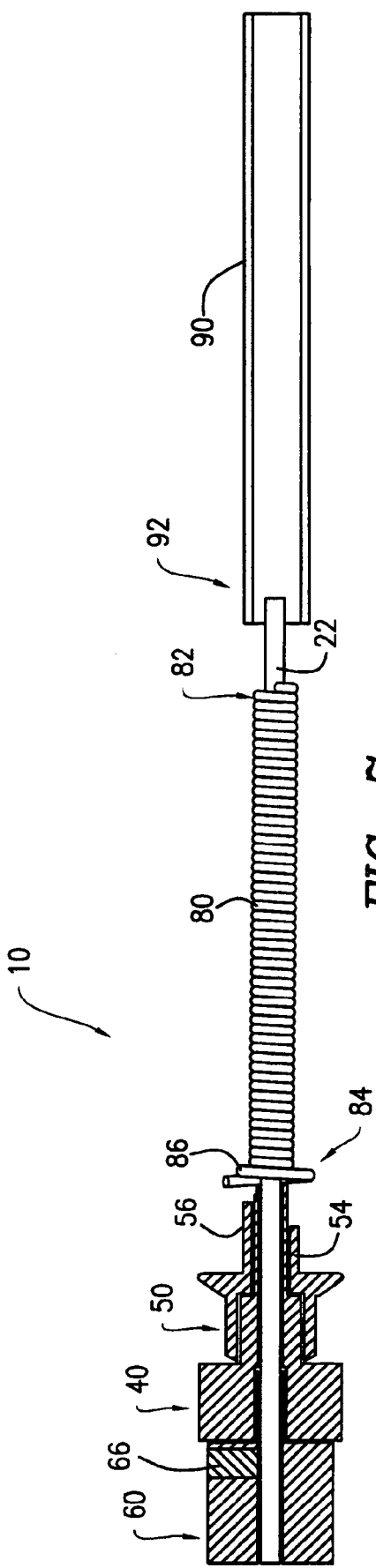
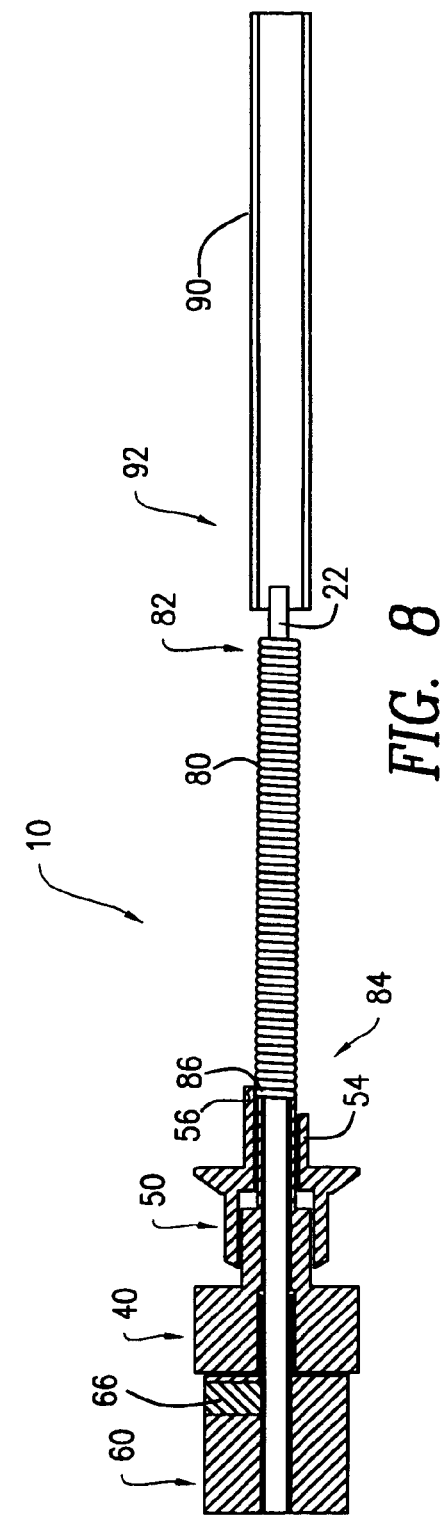

URETHRAL STENT REDUCER

FIELD OF THE INVENTION

The present invention relates to apparatus used for compressing a coiled stent and more particularly, for compressing a specific end portion of a stent prior to insertion either into an insertion apparatus or directly within the body.

BACKGROUND OF THE INVENTION

Lower urinary tract symptoms (LUTS), common among older men, include a variety of disorders that can lead to urinary retention and complications resulting from retention. Some of the conditions falling under a LUTS diagnosis include an enlarged prostate, BPH, and bladder outlet obstruction.

The constriction of the urethra due to prostatic enlargement can be treated by the implantation of a prostatic urethral stent. The stent serves to hold the prostatic urethra open to allow urination. This is typically an interim solution used before or after corrective treatment, e.g., a stent may be implanted after radiation treatments, thermal therapy or cryosurgery to keep the urethra open while post-treatment edema subsides. In some instances, a stent may be implanted as a primary treatment.

Generally, urethral stents are tubular in shape and may be in the form of a solid tube, coiled wire, ribbon or mesh, or formed from braided filaments. Coiled stents may be designed to have at least a portion thereof with outer diameter equal to or larger than the average urethral lumen diameter, such that when expanded, the stent frictionally engages the urethra into which it has been inserted. The larger diameter coils of such stents need to be radially compressed prior to insertion into a stent delivery system, e.g., a catheter sheath, or within the urethra. After being positioned in the urethra, urethral stents are radially expanded into their final shape, typically by thermal or mechanical means, or, in the case of self-expanding stents, allowed to elastically expand when a sheath or other restraining means is removed.

Brenneman et al. (U.S. Pat. No. 5,160,341) disclose a device including a retractable sheath surrounding a rotatable rod journaled in a stationary tubular bushing. One end of the stent is mounted on the rod while the other end of the stent is fixed to the bushing so that relative rotation of the rod and bushing compresses the entire stent by coiling it more tightly. After insertion within the body, the rod and bushing are then rotated in the opposite direction to uncoil the stent to its original diameter. A shearing sleeve with a shearing edge is advanced between the rod and bushing to sever the stent from its attachment to the bushing and the rod.

In the above device, both ends of the stent are used to engage the urethra and the diameter along the entire stent length is reduced. Reduction of stent diameter results in a concomitant increase in length in the reduced region. Reduction of stent diameter along the entire stent length will therefore result in significant length increases upon diameter reduction, sizing, bunching, and consequent placement issues within the anatomy. In some coil stent designs, only an end portion of the stent has a varying diameter. It is undesirable, particularly with polymer stents, to expose a stent to unnecessary forces due to risk of plastic deformation or creep. There are also risks associated with introducing a shearing sleeve with shearing edge within the urethra e.g. breakage, contamination and/or injury. In addition, the cut ends of the stent are sharp and pose a risk of penetrating the urethra.

Yachia et al. (U.S. Pat. No. 5,246,445) disclose stents with non-uniform windings such that one or more coils along the length of the stent bulge out circumferentially. An apparatus is disclosed which fixes either end of the stent and through torquing action, radially compresses the bulges. Here again, the entire length of the stent is reduced by rotating the ends of the helical spiral in opposite directions. A small hook, ring, or ball is provided at each end of the stent for grasping it. These features diminish uninterrupted flow capacity through the stent and increase the complexity of manufacture. Counter-rotation is required to release the stent.

Limon (U.S. Pat. No. 5,476,505) discloses a stent delivery system including a catheter formed from coaxially arranged inner and outer flexible shafts, the distal ends of which have slots or apertures to engage the ends of a coiled stent. The entire length of the stent is effected by inducing tighter coiling. The device is counter-rotated to expand and release the stent.

It would therefore be desirable to be able to radially compress selected regions of a coiled stent without compressing the entire stent. Such a device can be used to facilitate placement of the stent either within a secondary insertion tool or directly within the body.

SUMMARY OF THE INVENTION

The limitations of prior art apparatus for compressing stents are overcome by the present invention which includes an apparatus for compressing a coiled stent having at least one protrusion. The apparatus has a mandrel insertable into a lumen of the stent for holding the stent and a coil compressor coupled to the mandrel. The mandrel is rotatable on an axis relative to the coil compressor and the coil compressor has a tab extending therefrom towards the mandrel. The tab presses the protrusion of the stent inwardly toward the lumen of the stent when the mandrel is rotated relative to the coil compressor.

BRIEF DESCRIPTION OF THE FIGURES

The novel features of the present invention will be more readily apparent upon reading the following description in conjunction with the drawings in which like elements in different figures are identified by the same reference numeral and wherein:

FIG. 7 is a partial cross-sectional view of the stent reducer of FIGS. 1-6 taken along section line VII-VII looking in the direction of the arrows and with a stent on the mandrel prior to reduction of the distal stent diameter;

FIG. 8 is a cross-sectional view like FIG. 7, but after reduction of the distal stent diameter;

DETAILED DESCRIPTION OF THE INVENTION

Figure 1:
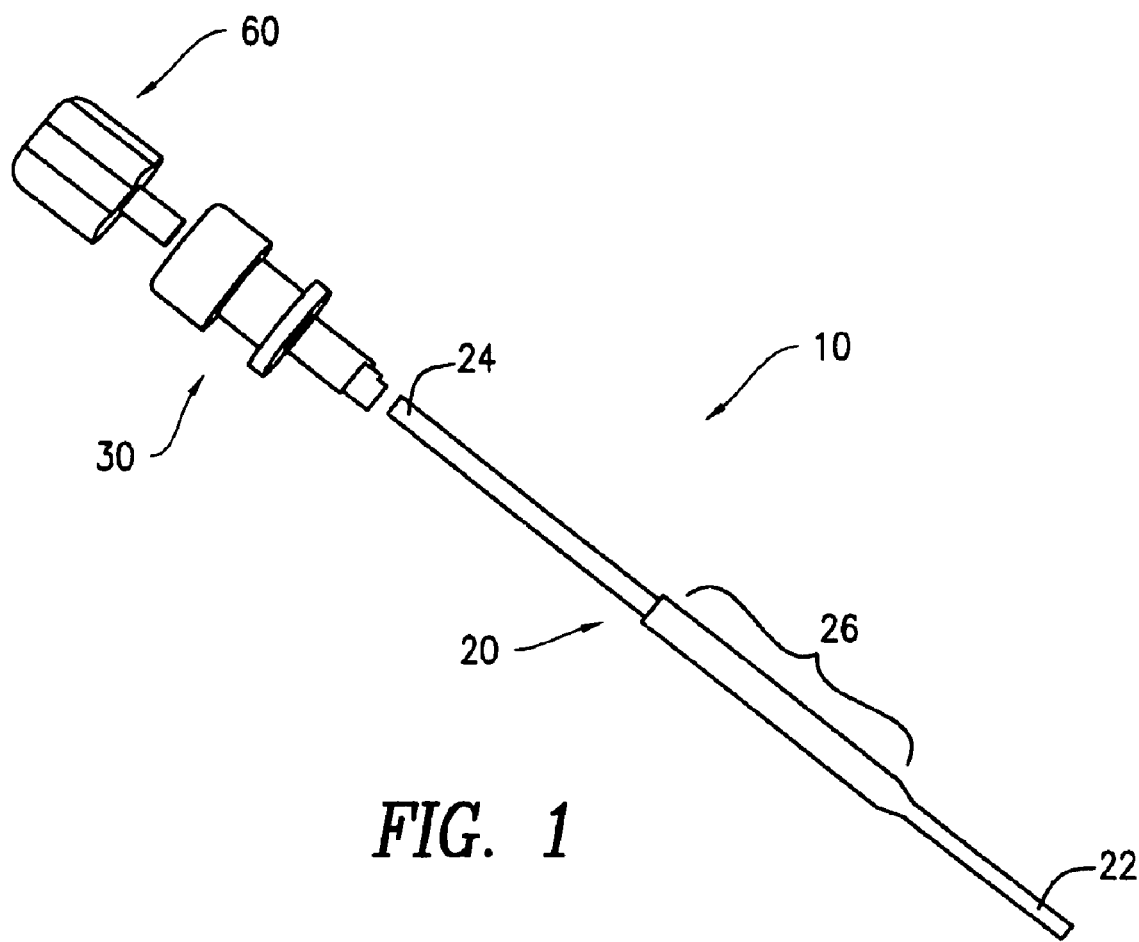
FIG. 1 is an exploded view of a stent reducer in accordance with an embodiment of the present invention.

FIGS. 1 through 9 show a stent reducer 10 for use in radially compressing selected larger diameter, radially-expanded coils 86 (See FIG. 6) of a coiled stent 80 without radially compressing the entire stent along its length. Stent 80 has a generally cylindrical coil shape, such as the stent described in U.S. patent application Ser. No. 10/602,338, entitled "Biodegradable stent", assigned to Ethicon Incorporated, filed Jun. 24, 2003, and incorporated herein by reference.

The stent 80 has a distal end 84 and a proximal end 82. Note that "proximal" and "distal" are reversed from the directionality of the stent reducer 10, because the convention applied to the stent 80 is relative to the bladder of the patient in which the stent 80 is placed. The diameter of the distal end 84 is greater than the remainder of the stent 80 due to radially expanded coil 86. While more than one complete turn of the coiled stent 80 is enlarged in FIG. 6, less than or greater than one complete turn of the stent 80 may be enlarged.

As shown in FIG. 1, stent reducer 10 has a mandrel 20 with a tapering distal end 22 which facilitates the insertion of the mandrel 20 into the lumen 81 (See FIG. 6) of the coiled stent 80, a proximal end 24 and a stent fixation zone 26. The diameter of the stent fixation zone 26 is the same as, or slightly larger than, the inner diameter of at least some portion of the stent 80, so that an interference fit is established between stent 80 and stent fixation zone 26 when the mandrel 20 is inserted into the stent 80. Preferably, the stent 80 can be rotated on the mandrel manually with minimal resistance. Since the stent 80 has a spiral shape, manual rotation of the stent 80 on the mandrel 20 can serve to advance the stent 80 over the mandrel 20 in threaded fashion. The surface of the stent fixation zone 26 may be textured to enhance the interference fit/thread-like interaction established between the stent 80 and stent fixation zone 26. The mandrel 20 may be one-piece or in a plurality of modular sections to accommodate various stent 80 sizes. The modular sections can be connected by conventional means, e.g., threads, snap-fit coupling, etc. A latch assembly 30 for compressing protrusions in the stent 80, such as expanded coils 86, slips over the proximal end 24 of the mandrel 20, as does mandrel knob 60.

Figure 2:
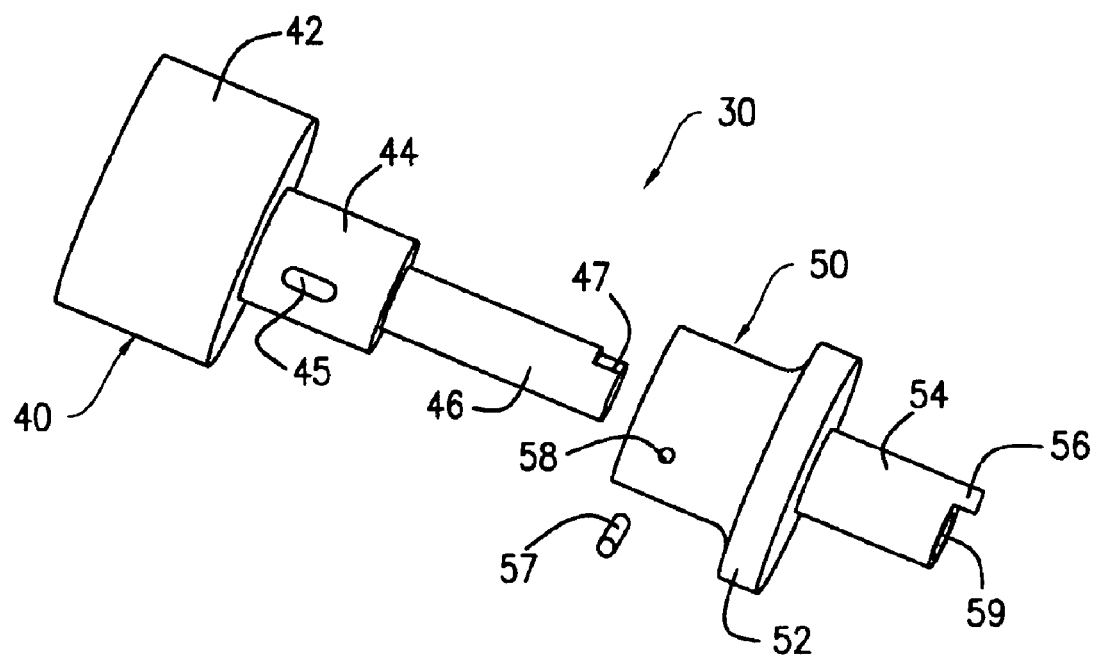
FIG. 2 is an exploded view of a latch assembly of the stent reducer of FIG. 1.

FIG. 2 shows an exploded view of latch assembly 30, which includes latch knob 40 and latch collar 50. The latch knob 40 has a grip portion 42, a hub portion 44 with a slot 45, and a post portion 46 with a relief 47. The latch knob 40 has an axial cannulation 41 into which the post 64 of mandrel knob 60 inserts and which also allows the mandrel 20 to extend through the latch knob 40. The latch knob 40 has ball plunger detents 49 on its proximal end (see FIG. 4). Latch collar 50 has a flange 52 against which the fingers of a user may press to control the position thereof. A pin 57 extends through hole 58 after the latch collar 50 is slidably and coaxially slipped onto the hub portion 44, the end of the pin 57 being accommodated in slot 45 and retaining the latch collar 50 on the latch knob 40 while permitting relative movement to the extent of the length of the slot 45. The latch collar 50 has a stepped internal bore 59 having internal dimensions approximating the external dimensions of the hub and post portions 44, 46 of the latch knob 40. A sleeve 54 extends from the flange 52 and has a distal tab 56 for contacting and compressing the stent 80.

Figure 3:
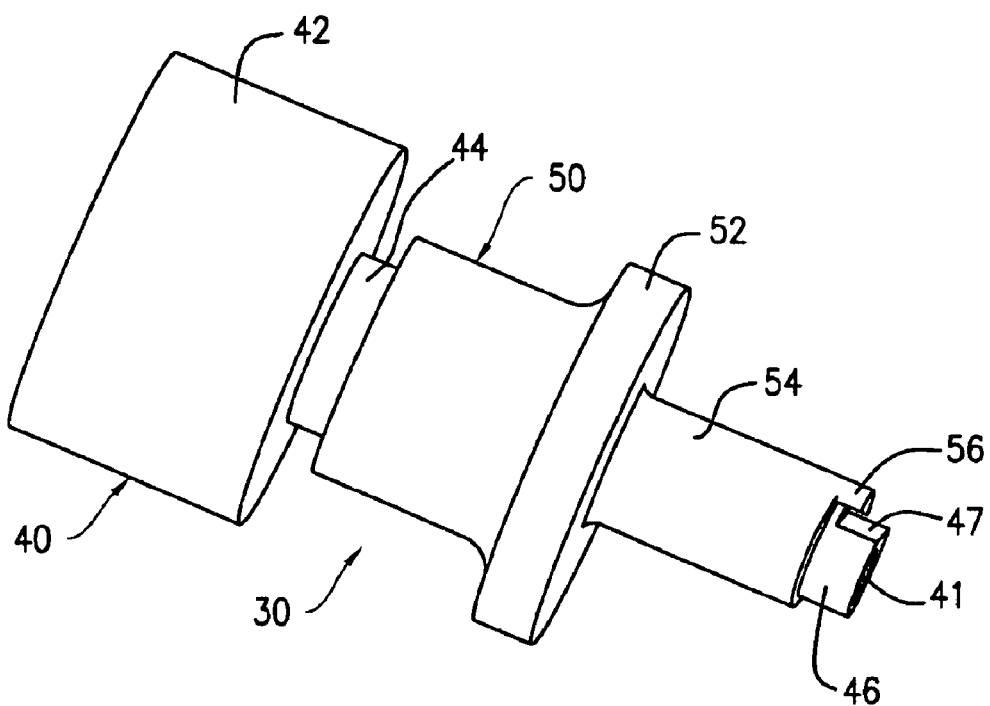
FIG. 3 is a perspective view of the latch assembly of FIG. 2.

As shown in FIG. 3, when assembled to form latch assembly 30, tab 56 overhangs relief 47. The length of slot 45 limits the range of axial motion of latch knob 40 in the distal direction to the point where tab 56 at least partially overhangs relief 47.

Figure 4:
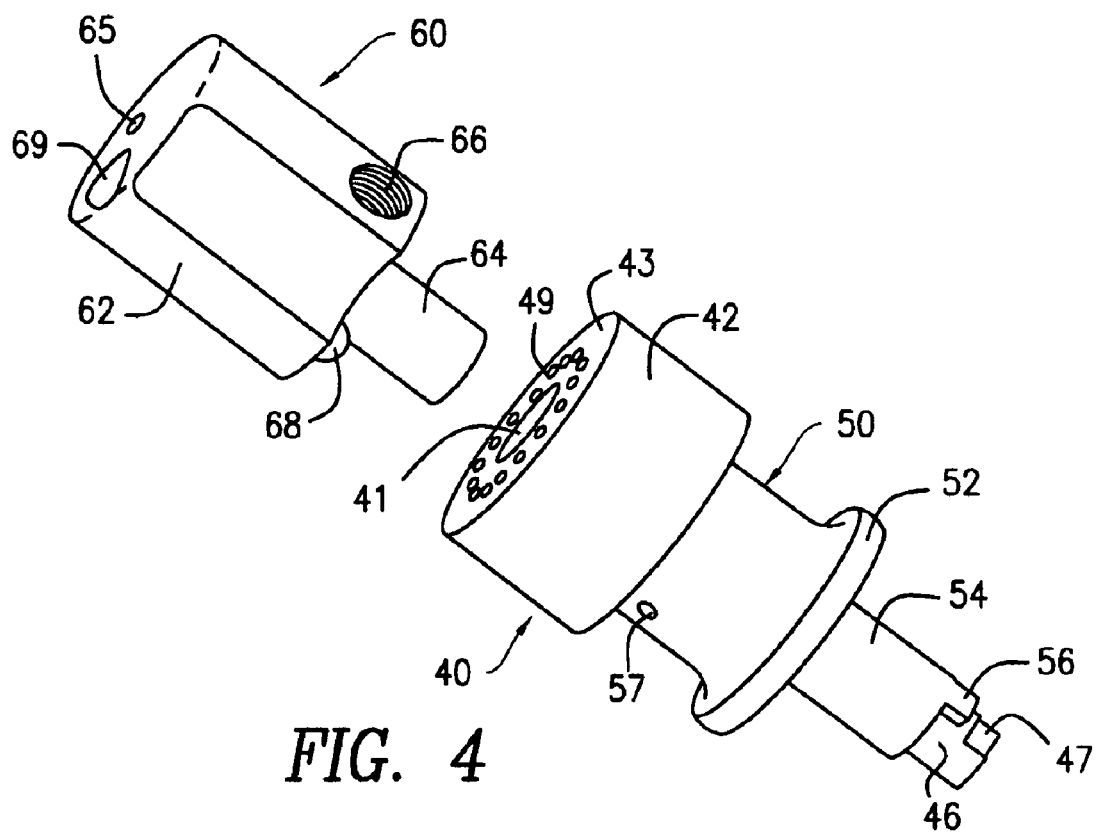
FIG. 4 is a partially exploded view of the latch assembly and mandrel knob of the stent reducer of FIGS. 1-3.

FIG. 4 shows mandrel knob 60, which has a grip portion 62 with a mandrel bore 65 for receiving proximal end 24 of mandrel 20 therein. The mandrel 20 is retained by a set screw (not shown) inserted into a threaded bore 66 and bearing upon the proximal end 24 thereof. A ball plunger 68 or similar spring-tape resilient member (not shown) is received within mating bore 69. Detents 49 are provided on a proximal surface 43 of latch knob 40 and receive the ball plunger 68 therein to control the axial rotation of mandrel knob 60 and mandrel 20 relative to the latch knob 40. FIG. 4 shows the latch knob 40 withdrawn to a proximal position wherein the tab 56 is retracted from relief 47.

Figure 5:
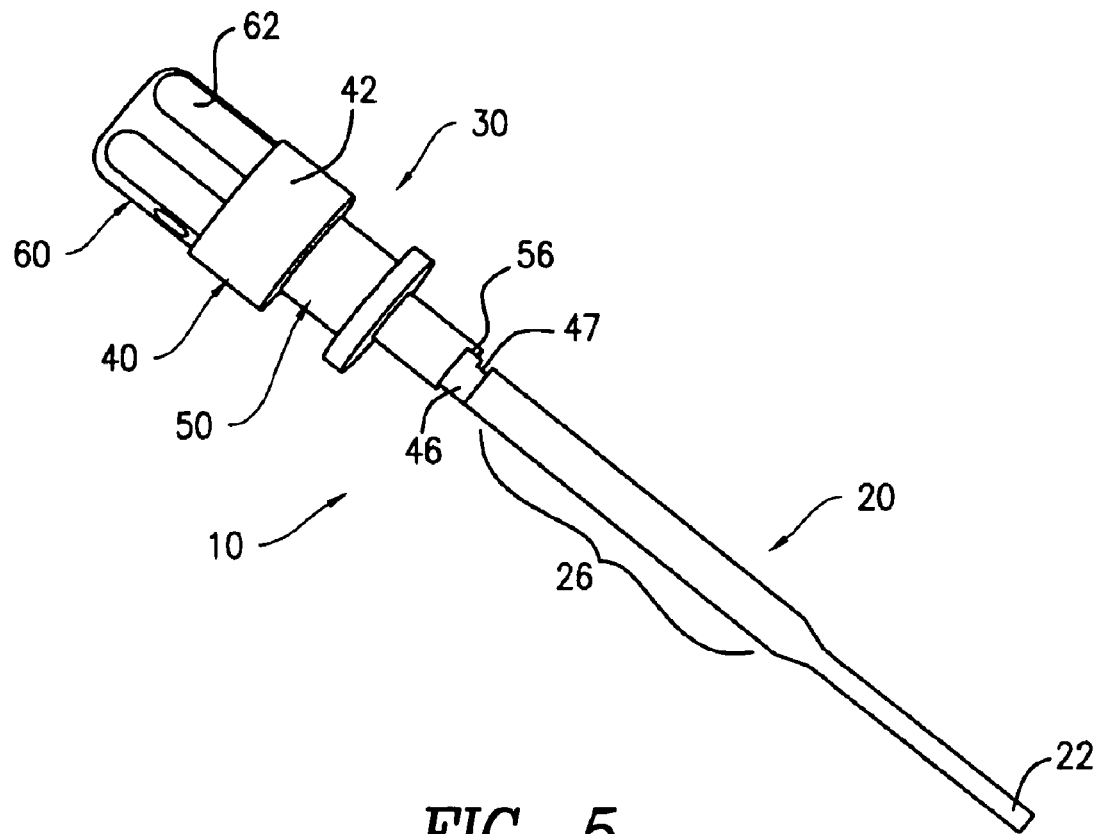
FIG. 5 is a perspective view of the stent reducer of FIGS. 1-4.

FIG. 5 shows the fully assembled stent reducer 10. The diameter of stent fixation zone 26 is approximately the same as the diameter of post portion 46. This prevents latch assembly 30 from sliding off of the mandrel 20.

Figure 6:
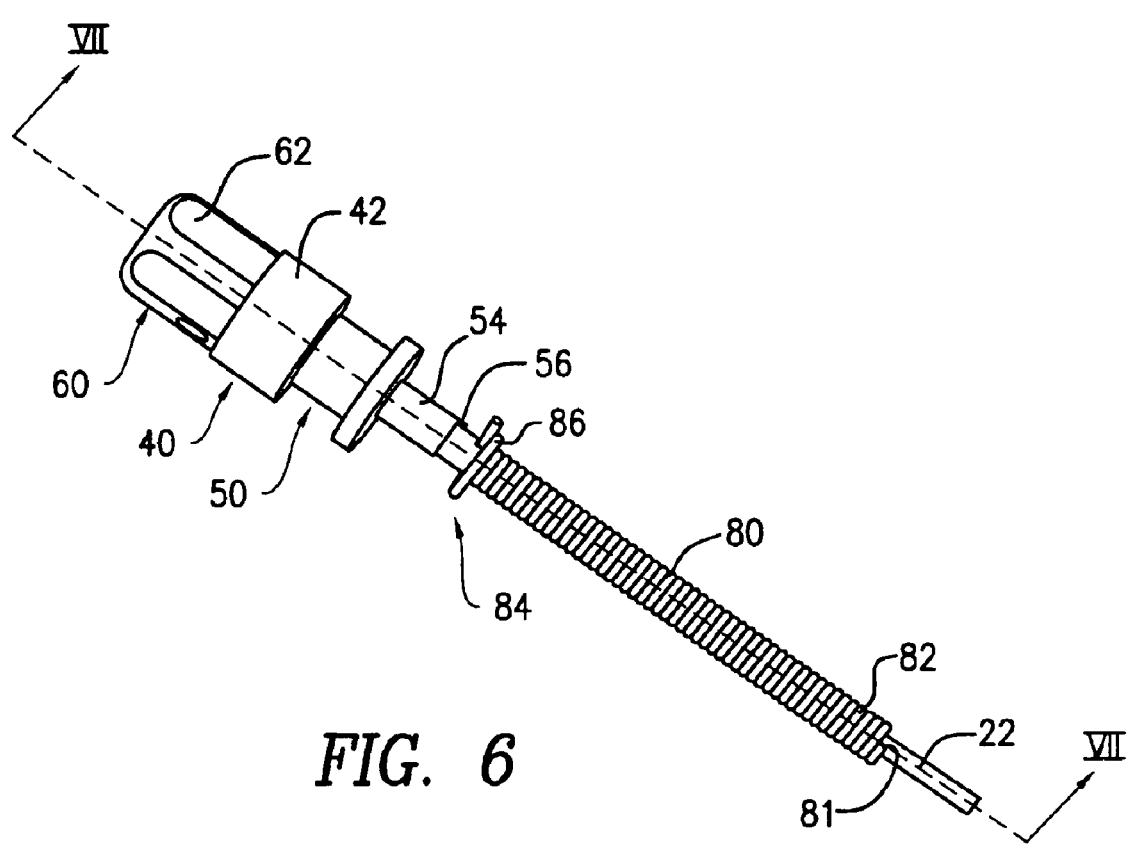
FIG. 6 is a perspective view of the stent reducer device of FIGS. 1-5 with a stent on the mandrel.
Figure 9:
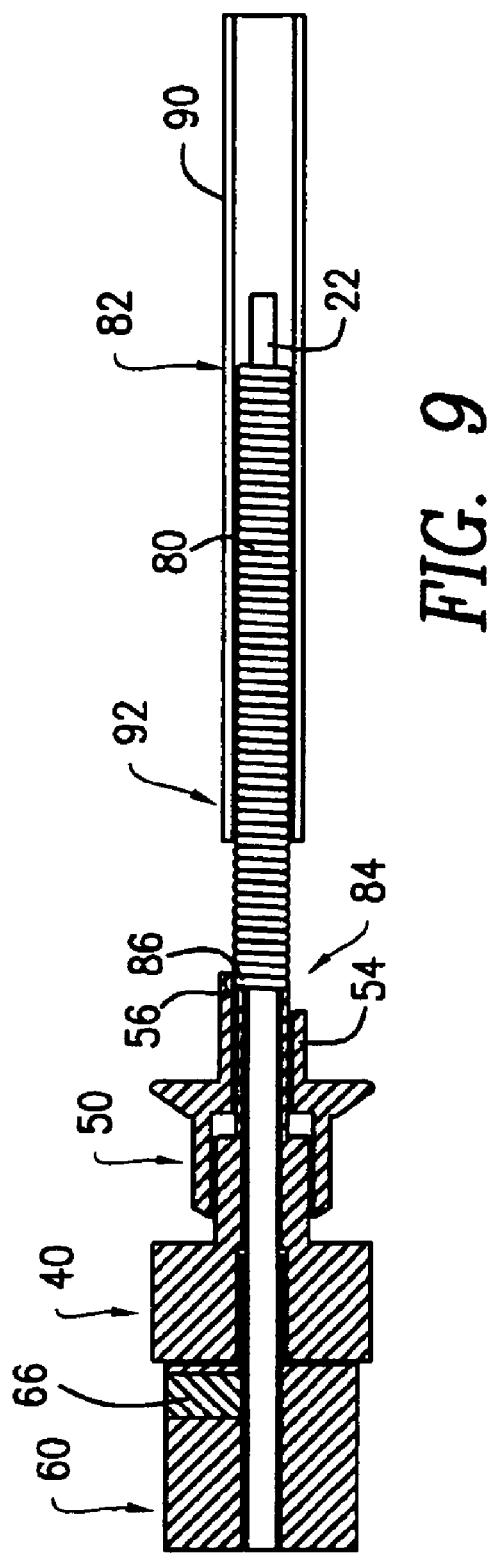
FIG. 9 is a cross-sectional view like FIG. 8 as the stent is being loaded into a sheath.

FIG. 6 shows a stent 80 in position on the mandrel 20 of stent reducer 10 prior to compression of radially expanded coils 86 on the distal end 84 of the stent 80.

FIGS. 7 through 10 show cross-sectional views of the stent reducer 10 and how it is used to reduce the diameter of the enlarged coils 86 at the distal end 84 of the stent 80, and load the stent 80 into a sheath 90. In FIG. 7, the mandrel 20 is inserted into the lumen of stent 80. The enlarged coils 86 of stent 80 distal end 84 are of a larger diameter than the remainder of the stent 80 and extend beyond the stent fixation zone 26 in the proximal direction. The latch collar 50 is positioned proximally on the latch knob 40 such that the tab 56 is retracted to a position removed from relief 47.

FIG. 8 shows the reduced distal end 84 of the stent 80 resulting from pushing the latch collar 50 forward, such that the tab 56 extends over an outer surface of the enlarged coil 86, capturing it between the tab 56 and the relief 47.

Figure 10:
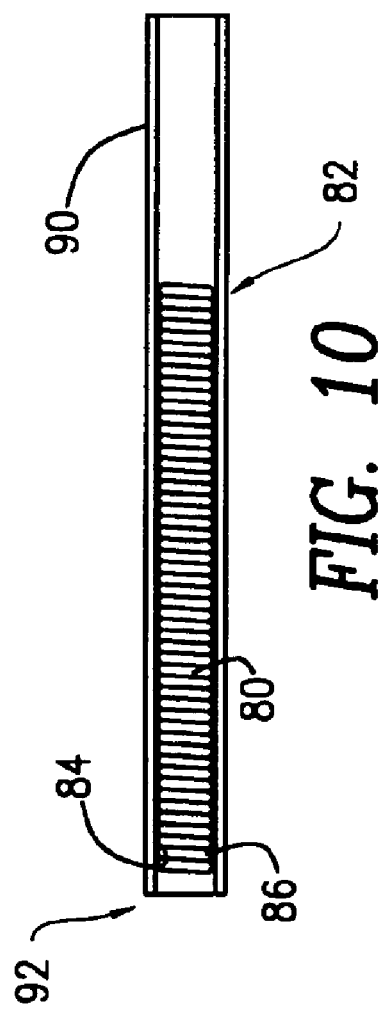
FIG. 10 is a cross-sectional view of the stent loaded into the sheath.

The user then grasps the mandrel knob 60 and the latch knob 40 and axially rotates the mandrel knob 60 relative to the latch knob 40 to reduce the diameter of the distal end 84 of stent 80. The ball plunger 68 and ball plunger detents 49 (FIG. 4) provide controlled relative rotation defining discrete tightening steps to avoid overrotation of stent 80. Once the outer diameter of the enlarged coils 86 are reduced, the stent 80 may be inserted into the sheath 90. When the stent 80 is fully inserted into sheath 90 i.e., beyond sheath proximal end 92, the user pulls the latch collar 50 proximally, releasing its hold on the enlarged coils 86 and permitting them to expand with the sheath exerting a frictional grip thereon. The mandrel 20 is then removed from the stent lumen 81, leaving the stent 80 disposed (loaded) in the sheath 90. FIG. 10 shows a stent 80 in a sheath 90 after removal of the mandrel 20.

We claim:

1. An apparatus for compressing a stent having at least one protrusion, comprising:

a mandrel insertable into a lumen of the stent for holding the stent;

a protrusion compressor coupled to said mandrel proximate a proximal end thereof, said mandrel extending axially into said protrusion compressor and being rotatable relative thereto;

a knob disposed on said mandrel proximate a proximal end thereof for retaining said protrusion compressor on said mandrel, said mandrel having a stent fixation zone with an outer diameter greater than an interior diameter of at least a portion of the lumen of the stent prior to installation of the stent on the mandrel and frictionally engaging the stent when the stent is placed on the mandrel over said stent retention zone to hold the stent on said mandrel, said protrusion compressor being captured between said knob and said stent retention zone, said protrusion compressor having a hub with a grip portion and a collar, said hub having a sidewall bounding an axial hollow into which said mandrel extends, said collar coaxially received on said hub and having a tab extending at a distal end thereof, said tab having an inwardly directed surface facing a central axis of said collar, said collar moveable telescopically on said hub between a retracted position and a deployed position, said hub having a relief slot on an exterior surface of said sidewall external to said hollow, said relief slot having an outwardly directed surface facing away from a central axis of said hub, said relief slot formed in said sidewall proximate a distal end thereof, said relief slot positioned on said hub to align with said tab, such that said inwardly directed surface of said tab and said outwardly directed surface of said relief slot face each other with a spacing there between for accommodating a portion of the stent when said collar is in the deployed position, said tab capturing the stent proximate a proximal end thereof between said inwardly directed surface of said tab and said outwardly directed surface of said relief slot, said apparatus compressing the at least one protrusion when said mandrel is rotated relative to said protrusion compressor while the stent is captured between said tab and said relief slot.

2. The apparatus of claim 1, wherein said mandrel extends through said protrusion compressor coaxially.

3. The apparatus of claim 2, wherein said grip portion has an enlarged diameter relative to an adjacent portion of said hub, said hub having a post portion with a diameter less than said hub and extending distally from said adjacent portion, said relief being provided on a side wall of said post portion, said collar having a stepped bore, with a first portion having a diameter approximating said adjacent portion of said hub and a second portion with a diameter approximating said post portion.

4. The apparatus of claim 3, wherein said stent fixation zone has an outer diameter approximating a diameter of said post portion.

5. The apparatus of claim 4, wherein said mandrel has a tapered end leading to said stent retention zone, said tapered end aiding in inserting the mandrel into the lumen of the stent and sliding the stent on to the stent retention zone.

6. The apparatus of claim 4, wherein said protrusion compressor is captured between said knob and said stent retention zone.

7. The apparatus of claim 1, wherein said collar is restrained from rotating relative to said grip portion by a pin extending there through and into an elongated slot in said hub, said slot and pin constraining the collar to telescopic movement on said hub along a length of travel limited by said slot.

8. The apparatus of claim 7, wherein said collar has a flange extending outwardly therefrom for a user to grip said collar to aid in deployment and retraction of said tab.

9. An apparatus for compressing a stent having at least one protrusion, comprising:
a mandrel insertable into a lumen of the stent for holding the stent;
a protrusion compressor coupled to said mandrel, said mandrel rotatable relative to said protrusion compressor, said protrusion compressor having a tab extending therefrom towards said mandrel, said tab pressing the at least one protrusion of the stent inwardly toward the lumen of the stent when said mandrel is rotated relative to said protrusion compressor, said mandrel extending through said protrusion compressor coaxially;
a knob disposed on an end of said mandrel to aid in turning said mandrel and for retaining said protrusion compressor on said mandrel, said mandrel having a stent fixation zone with an outer diameter greater than the interior diameter of at least a portion of the lumen of the stent prior to installation of the stent on the mandrel and frictionally engaging the stent when the stent is placed on the mandrel over the stent retention zone to hold the stent on the mandrel, said protrusion compressor being captured between said knob and said stent retention zone, said protrusion compressor having a hub with a grip portion and a hollow post portion and a collar, said collar coaxially received on said hub and having said tab extending therefrom at a distal end thereof, said tab having an inwardly directed surface facing a central axis of said collar, said collar restrained from rotating relative to said grip portion by a pin extending there through and into an elongated slot in said hub, said slot and pin constraining the collar to telescopic movement on said hub along a length of travel limited by said slot and defining a retracted position and a deployed position for said tab, said collar having a flange extending outwardly therefrom for a user to grip said collar to aid in deployment and retraction of said tab, said hollow post portion having a relief slot with an outwardly directed surface facing away from a central axis of said hub and formed on an exterior sidewall thereof distal to a hollow within said hollow post portion and proximate a distal end thereof, said relief slot positioned on said hollow post portion to align with said tab when said tab is in the deployed position, such that said inwardly directed surface of said tab and said outwardly directed surface of said relief slot face each other with a spacing there between for accommodating a portion of the stent, said tab capturing the stent proximate a proximal end thereof between said inwardly directed surface of said tab and said outwardly directed surface of said relief slot when said apparatus compresses the at least one protrusion.

10. The apparatus of claim 9, further including a ball and detent interface disposed between said grip portion and said knob, said ball and detent interface controlling the relative rotation between said grip portion and said knob.

11. The apparatus of claim 10, wherein the at least one protrusion of the stent is at least one enlarged coil disposed at an end of the stent, said apparatus pressing the enlarged coil inwardly by pushing said collar portion forward to the deployed position to capture said enlarged coil between said tab and said relief slot and turning the knob and the mandrel relative to said protrusion compressor.

12. The apparatus of claim 11, further including a sleeve extending from said collar distal to said flange, said tab extending from said sleeve.

* * * * *